United States Patent [19]
Bartorelli et al.

[11] Patent Number: 6,107,474
[45] Date of Patent: Aug. 22, 2000

[54] NUCLEOTIDE SEQUENCE ENCODING A 14 KDA PROTEIN FROM GOAT LIVER

[75] Inventors: Alberto Bartorelli; Bruno Berra; Irma Colombo; Severino Ronchi, all of Milan, Italy

[73] Assignee: Zetesis S.p.A, Milan, Italy

[21] Appl. No.: 09/125,265

[22] PCT Filed: Feb. 11, 1997

[86] PCT No.: PCT/EP97/00611

§ 371 Date: Aug. 12, 1998

§ 102(e) Date: Aug. 12, 1998

[87] PCT Pub. No.: WO97/30154

PCT Pub. Date: Aug. 21, 1997

[30] Foreign Application Priority Data

Feb. 13, 1996 [IT] Italy .................................. MI96A0264

[51] Int. Cl.$^7$ ..................................................... C07H 21/04
[52] U.S. Cl. ................... 536/23.5; 536/24.31; 536/24.33
[58] Field of Search ................................ 536/23.5, 24.31, 536/24.33

[56] References Cited

FOREIGN PATENT DOCUMENTS

92/10197  6/1992  WIPO .
96/02567  2/1996  WIPO .

OTHER PUBLICATIONS

Schmiedeknecht et al., Eur. J. Biochem. 242, 339–351 (Dec. 1996).
Colombo et al., Biochim. Biophys. Acta 1442, 49–59 (1998).
Levy Favatier et al., Eur. J. Biochem. 212, 665–673 (1993).
Journal of Biological Chemistry, vol. 270, No. 50, Dec. 15, 1995, pp. 30060–30067, XP002031276, T. Oka et al, "Isolation and Characterization of a Novel Perchloric Acid–soluble Protein Inhibiting . . . ".
FEBS Letters, vol. 393, No. 2,3, Sep. 16, 1996, pp. 147–150, XP002031277, F. Ceciliani et al, "The primary structure of UK114 tumor antigen".

*Primary Examiner*—Kenneth R. Horlick
*Attorney, Agent, or Firm*—Birch, Stewart, Kolasch & Birch, LLP

[57] ABSTRACT

A complete cDNA sequence (SEQ ID NO: 1) is described, which codes for a 14 kDa protein (SEQ ID NO: 2) obtainable from goat liver. This protein shows marked antineoplastic activity both in vitro and in vivo. The serum of animals immunized with this protein displays cytotoxic activity against human tumor cell lines. The cDNA sequence of the invention may be obtained by procedures involving, among other things, the use of degenerate oligonucleotides.

1 Claim, No Drawings

6,107,474

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1017 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Capra hircus
      (F) TISSUE TYPE: Liver (ix) FEATURE:
      (A) NAME/KEY: CDS
      (B) LOCATION:101..511

(xi) SEQUENCE DESCRIPTION: SEQ ID NO: 1:

```
CTTTGAAGCA GCGATTCTGG CTTCGGCTGG TCAGGCGACG CGAGCAGAAC CGTGTGCTGC      60

GTACTTGTTT CCGAAGGGCA GCAAAGGAAA AGGGTTAGCC ATG TCG TCT TTG GTC      115
                                            Met Ser Ser Leu Val
                                              1               5

AGA AGG ATA ATC AGC ACG GCG AAA GCC CCC GCG GCC ATT GGT CCC TAC      163
Arg Arg Ile Ile Ser Thr Ala Lys Ala Pro Ala Ala Ile Gly Pro Tyr
                10                  15                  20

AGT CAG GCT GTG TTA GTC GAC AGG ACC ATT TAC ATT TCA GGA CAG CTA      211
Ser Gln Ala Val Leu Val Asp Arg Thr Ile Tyr Ile Ser Gly Gln Leu
             25                  30                  35

GGT ATG GAC CCT GCA AGT GGA CAG CTT GTG CCA GGA GGG GTG GTA GAA      259
Gly Met Asp Pro Ala Ser Gly Gln Leu Val Pro Gly Gly Val Val Glu
         40                  45                  50

GAG GCT AAA CAG GCT CTT ACA AAC ATA GGT GAA ATT CTG AAA GCA GCA      307
Glu Ala Lys Gln Ala Leu Thr Asn Ile Gly Glu Ile Leu Lys Ala Ala
     55                  60                  65

GGC TGT GAC TTC ACG AAT GTG GTA AAA GCA ACG GTT TTG CTG GCT GAC      355
Gly Cys Asp Phe Thr Asn Val Val Lys Ala Thr Val Leu Leu Ala Asp
 70                  75                  80                  85

ATA AAT GAC TTC AGT GCT GTC AAT GAT GTC TAC AAA CAA TAT TTC CAG      403
Ile Asn Asp Phe Ser Ala Val Asn Asp Val Tyr Lys Gln Tyr Phe Gln
                 90                  95                 100

AGT AGT TTT CCG GCG AGA GCT GCT TAC CAG GTT GCT GCT TTG CCC AAA      451
Ser Ser Phe Pro Ala Arg Ala Ala Tyr Gln Val Ala Ala Leu Pro Lys
            105                 110                 115

GGA GGC CGT GTT GAG ATC GAA GCA ATA GCT GTG CAA GGA CCT CTC ACG      499
Gly Gly Arg Val Glu Ile Glu Ala Ile Ala Val Gln Gly Pro Leu Thr
        120                 125                 130

ACA GCA TCA CTC TAAGTGGGCC AAGTGTTATT TAGTCTGGAA ATTTAATAGT          551
Thr Ala Ser Leu
        135

ATTTTTAAAC TAATGGCTTA ATCCTTGTTG GAAAGTATTA AGGTTGAAAT ATCTGAAAAT    611

ATTATGGAAA TACCATATAA TAAGGGAAAC GATATGAATT GAAGATTAAT GATGAATCTA    671
```

```
GTTACTAATA TTACAAATTA TACTTCTGTA ACACTTGTAT TGCTGGATGT GGGAAAACAG    731

ACATGCCTTA CTGAGTTAAC TCAGAAGAAT AAAAGTAGAA GGAAATAACA TGTAGGAAAG    791

ATGAGCTACT ATGCCTGAAA AGTAAGGAAA AGCACACCTA ATTCAACTAA ACCCTATTAA    851

TTTAATGATG GGAAGTATTT TATTATGTCA GATATGTGAT TTTTACTTGA ATAAAACTAA    911

AGCATTTAAA TTTGAATGGC AGAGATAAAG GAGAAGAAAC TGGACCAAAT TTTATATAGA    971

TAATATTTTT CTAGTGGAAA TAAAATAGCA TGCAGATTTT CAAAAA                   1017
```

(2) INFORMATION FOR SEQ ID NO: 2:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Ser Leu Val Arg Arg Ile Ile Ser Thr Ala Lys Ala Pro Ala
 1               5                  10                  15

Ala Ile Gly Pro Tyr Ser Gln Ala Val Leu Val Asp Arg Thr Ile Tyr
            20                  25                  30

Ile Ser Gly Gln Leu Gly Met Asp Pro Ala Ser Gly Gln Leu Val Pro
        35                  40                  45

Gly Gly Val Val Glu Glu Ala Lys Gln Ala Leu Thr Asn Ile Gly Glu
    50                  55                  60

Ile Leu Lys Ala Ala Gly Cys Asp Phe Thr Asn Val Val Lys Ala Thr
65                  70                  75                  80

Val Leu Leu Ala Asp Ile Asn Asp Phe Ser Ala Val Asn Asp Val Tyr
                85                  90                  95

Lys Gln Tyr Phe Gln Ser Ser Phe Pro Ala Arg Ala Ala Tyr Gln Val
            100                 105                 110

Ala Ala Leu Pro Lys Gly Gly Arg Val Glu Ile Glu Ala Ile Ala Val
            115                 120                 125

Gln Gly Pro Leu Thr Thr Ala Ser Leu
    130                 135
```

NUCLEOTIDE SEQUENCE ENCODING A 14 KDA PROTEIN FROM GOAT LIVER

The present invention refers to a cDNA sequence encoding a 14 kDa protein from goat liver.

WO 92/10197 discloses perchloric acid extracts of mammalian organs, in, particular of goat liver, consisting of at least three different proteins and characterized by unusual pharmacological and immunological properties.

More recently, in WO 96/02567, the partial aminoacid sequence of a 14 kDa protein purified from the extracts disclosed in WO 92/10197 has been described. This protein shows marked antineoplastic activity either in vitro and in vivo and the serum of animals immunized with this protein displays cytotoxic activity against human tumor cell lines.

In 1993, Levy-Favatier et al. [*Eur. J. Biochem.* 212 (3), 665–673] have reported the cDNA sequence coding for a 23 kDa dimeric protein purified by 5% perchloric acid from rat liver and kidney; the corresponding aminoacid sequence shows an high degree of homology with the sequence of the 14 kDa protein disclosed in WO 96/02567. The cDNA sequence has been submitted to the EMBL Data Bank with Accession no. X70825.

In 1995, another cDNA sequence coding for a 14 kDa protein purified by perchloric acid from rat liver, with an high degree of homology with that published by Levy-Favatier et al., has been submitted to the EMBL Data Bank with Accession no. D49363. This sequence has been reported by Oka et al. in *J. Biol. Chem.* (1995) 270 (50), 30060–30067.

Furthermore, in 1996, two novel mRNA sequences with an high degree of homology with the cDNA published by Levy-Favatier et al. and by Oka et al. have been submitted to the EMBL Data Bank. One of these (Accession no: X95384) codes for a 14.5 kDa human protein and it has been recently published by Schmiedeknecht et al. [*Eur. J. Biochem.* (1996) 242 (2), 339–351]. The other sequence (Accession no: U50631) codes a "Mus Musculus heat-responsive protein"; up to now, no extensive paper concerning this sequence has been published.

We have now found a new cDNA sequence, encoding the entire 14 kDa protein extracted by perchloric acid from goat liver and disclosed in WO 96/02567. The complete nucleotide sequence is reported in SEQ ID NO: 1.

The cDNA sequence coding for the 14 kDa protein extracted by perchloric acid from goat liver and disclosed in WO 96/02567 (SEQ ID NO: 2), is useful for the preparation of said protein or of muteins thereof by means of recombinant DNA methods or for diagnostic applications based on nucleotide probes.

The cDNA sequence of the invention has been obtained by the following method: two mixtures of degenerate oligonucleotides have been synthesized on the basis of the aminoacid sequence disclosed in WO 96/02567. One mixture (named PG-1) consists of 2.048 oligo-20-mers, corresponding to aminoacid sequence extending from Met-1 to Gln-7. The other mixture (named PG-2) consists of 192 oligo-20-mers corresponding to aminoacid sequence extending from Ala-46 to Xaa-52.

Using these oligonucleotide mixtures as primers and cDNAs obtained by reverse transcription of total RNA purified from goat liver as template, a PCR reaction has been performed. The reverse transcription reaction has been carried out at 42° C. for 60 min. using oligo(dT)$_{15}$ as primer. After 35 cycles of amplification at the following conditions: 95° C. for 2 min.–55° C. for 2 min.–72° C. for 1 min. in 2 mM MgCl$_2$, the DNA fragment amplified (155 bp) has been subcloned in the plasmid vector pCRII and the insert of three different clones has been sequenced using T7 and Sp6 sequencing primers. The nucleotide sequence of this fragment (corresponding to region extending from nt. 215 to nt. 369 of the Sequence Id n. 1) confirms the aminoacid sequence disclosed in WO 96/02567 and identifies the Xaa-33 as Cys.

After the characterization of the complete aminoacid sequence of the 14 kDa protein reported by Ceciliani et al. [*FEBS Lett.* (1996) 393, 147–150] and following a procedure similar to that described above, the nucleotide sequence extending from nt. 215 to nt. 511 of the SEQ ID NO: 1 has been determined. Briefly, degenerate oligonucleotides (named PG-9) have been synthesized. This mixture consists of 32.768 oligo-20-mers corresponding to aminoacid sequence extending from Pro-131 to Val-137. Using the oligonucleotide mixtures named PG-1 and PG-9 as primers and cDNAs obtained by reverse transcription of total RNA purified from goat liver as template, the PCR reaction has been performed in the same previous conditions. The amplified DNA fragment of 296 bp has been subcloned in the plasmid vector pCRII and the insert has been sequenced using T7 and Sp6 sequencing primers.

The nucleotide sequence extending towards poly(A) tail has been found by 3'-rapid amplification cDNA end (3'-RACE) method suitably modified. In this case, the template used in the PCR reaction has been obtained by reverse transcription of total RNA purified from goat liver using as primer an adaptor linked-oligo(dT)$_{17}$. The PCR primers were represented by the adaptor and by an oligo-30-mer (named PG-4) located on the region extending from nt. 236 to nt. 265. Conditions of the PCR reaction were the following: the reaction mixture containing 2 mM MgCl$_2$ and only the primer named PG-4 has been subjected to 10 cycles of amplification of two steps: 95° C. for 45 sec.–72° C. for 3 min. Then, after the addition of the second PCR primer (the adaptor), 35 cycles of amplification have been performed at the following conditions: 95° C. for 45 sec.–52° C. for 1 min.–72° C. for 2 min. To isolate a more discrete DNA fragment, a successive nested-PCR has been performed using a downstream primer named PG-5 extending from nt. 266 to nt. 289 of the SEQ ID NO: 1. Also this DNA fragment (about 800 bp) has been subcloned in the plasmid vector pCRII and sequenced with T7 and Sp6 sequencing primers. Its nucleotide sequence confirms the aminoacid sequence from Lys-56 towards C-terminal of the 14 kDa protein described by Ceciliani et al. [*FEBS Lett.* (1996) 393, 147–150], except for the last aminoacid: Val-137 is substituted by Leu-137.

The nucleotide sequence extending towards the 5'-end of the cDNA has been found by 5'-RACE method. This procedure consists in the synthesis of double-strand cDNAs from RNA poly(A) extracted from goat liver, ligation of these cDNAs with an adaptor and amplification by PCR using a primer located on the adaptor sequence and the other primer located on the cDNA sequence to be extended. In this specific case, the primer extending from nt. 290 to nt. 316 of the Sequence Id n. 1 has been used. The DNA fragments (about 300 bp) obtained have been subcloned in the plasmid vector pCRII and sequenced with T7 and Sp6 sequencing primers.

The entire cDNA sequence has been finally confirmed by direct DNA sequencing performed on two DNA fragment obtained by two different PCR reaction. As previously, DNA template was cDNAs obtained by reverse trascription of total RNA from goat liver using oligo (dT)$_{15}$ as primer, and the two primers for the amplification were located on the 5'-end extending from nt. 1 to nt. 26 of the Sequence Id n. 1 and on the 3'-end extending from nt. 984 to nt. 1007 of the SEQ ID NO: 1 of the cDNA. After 35 cycles of amplification at the following conditions: 95° C. for 45 sec.–60° C. for 45 sec.–72° C. for 1 min. 30 sec. in 2 mM MgCl$_2$, the DNA fragment of 1007 bp was subjected to direct sequencing following the standard procedure indicated in the kit's instructions.

What is claimed is:

1. The cDNA sequence of SEQ ID NO:1.

\* \* \* \* \*